United States Patent
Solomon et al.

(10) Patent No.: US 7,988,996 B2
(45) Date of Patent: *Aug. 2, 2011

(54) PHARMACEUTICAL TABLETS WITH HEIGHT GREATER THAN WIDTH

(75) Inventors: Lawrence Solomon, Boca Raton, FL (US); Allan S. Kaplan, Boca Raton, FL (US)

(73) Assignee: Accu-Break Technologies, Inc., Plantation, FL (US)

( * ) Notice: Subject to any disclaimer, the term of this patent is extended or adjusted under 35 U.S.C. 154(b) by 488 days.

This patent is subject to a terminal disclaimer.

(21) Appl. No.: 11/561,968

(22) Filed: Nov. 21, 2006

(65) Prior Publication Data

US 2007/0134321 A1 Jun. 14, 2007

Related U.S. Application Data

(63) Continuation-in-part of application No. 11/569,343, filed as application No. PCT/US2005/018633 on May 23, 2005.

(60) Provisional application No. 60/573,042, filed on May 21, 2004, provisional application No. 60/573,134, filed on May 21, 2004.

(51) Int. Cl.
| | |
|---|---|
| *A61K 9/20* | (2006.01) |
| *A61K 9/22* | (2006.01) |
| *A61K 9/24* | (2006.01) |
| *A61K 9/26* | (2006.01) |
| *A61K 9/28* | (2006.01) |
| *A61K 9/44* | (2006.01) |

(52) U.S. Cl. ........ 424/464; 424/467; 424/468; 424/469; 424/472; 424/474

(58) Field of Classification Search .................. None
See application file for complete search history.

(56) References Cited

U.S. PATENT DOCUMENTS

| | | | |
|---|---|---|---|
| 3,128,226 A | | 4/1964 | Rubin et al. |
| 4,905,589 A | * | 3/1990 | Ackley ............................ 101/35 |
| 5,118,021 A | * | 6/1992 | Fiocchi ......................... 225/103 |
| 5,158,728 A | | 10/1992 | Sanderson |
| 5,478,901 A | | 12/1995 | Jones et al. |
| 5,817,340 A | | 10/1998 | Roche et al. |
| 6,086,919 A | | 7/2000 | Bauer et al. |
| 6,161,260 A | | 12/2000 | Flewitt |
| 6,183,778 B1 | | 2/2001 | Conte et al. |
| 6,294,200 B1 | | 9/2001 | Conte et al. |
| 6,309,668 B1 | | 10/2001 | Bastin et al. |
| 6,919,373 B1 | | 7/2005 | Lam et al. |
| 7,011,849 B2 | | 3/2006 | Storm et al. |
| 7,318,935 B2 | * | 1/2008 | Solomon et al. .............. 424/464 |
| 7,329,418 B2 | * | 2/2008 | Solomon et al. .............. 424/464 |
| 2002/0012675 A1 | * | 1/2002 | Jain et al. ....................... 424/400 |
| 2002/0132850 A1 | | 9/2002 | Bartholomaus et al. |
| 2005/0013863 A1 | | 1/2005 | Lim et al. |
| 2005/0038039 A1 | | 2/2005 | Fanara et al. |
| 2006/0280794 A1 | | 12/2006 | Hamaguchi et al. |

FOREIGN PATENT DOCUMENTS

| | | | |
|---|---|---|---|
| EP | 348683 A1 | * | 1/1990 |
| JP | 06009375 A | * | 1/1994 |

OTHER PUBLICATIONS

Pharmaceutical Industry.Info (2002)(http://www.pharmaceutical-industry.info/modules/pharmaceutical_suppliers/korsch/korsch-products.html), p. 2.*

* cited by examiner

*Primary Examiner* — Sreeni Padmanabhan
*Assistant Examiner* — Frank Choi
(74) *Attorney, Agent, or Firm* — Ted W. Whitlock

(57) ABSTRACT

Described is a compressed multiple layer pharmaceutical tablet that has a height that exceeds the width of the tablet. The height is measured vertically from the top to the bottom of the tablet while it is in the tablet die in which it is fully compressed, after compression has been completed. The width is measured as the greatest horizontal dimension of the tablet at a location halfway between the top and the bottom of the tablet, except that when the horizontal cross-section of the tablet is substantially rectangular, the width is defined by locating the two shorter sides of the perimeter of the horizontal cross-section, and measuring the length of a line that is at right angle to the shorter sides. The layers can form a segment or, preferably, more than one segment.

31 Claims, 8 Drawing Sheets

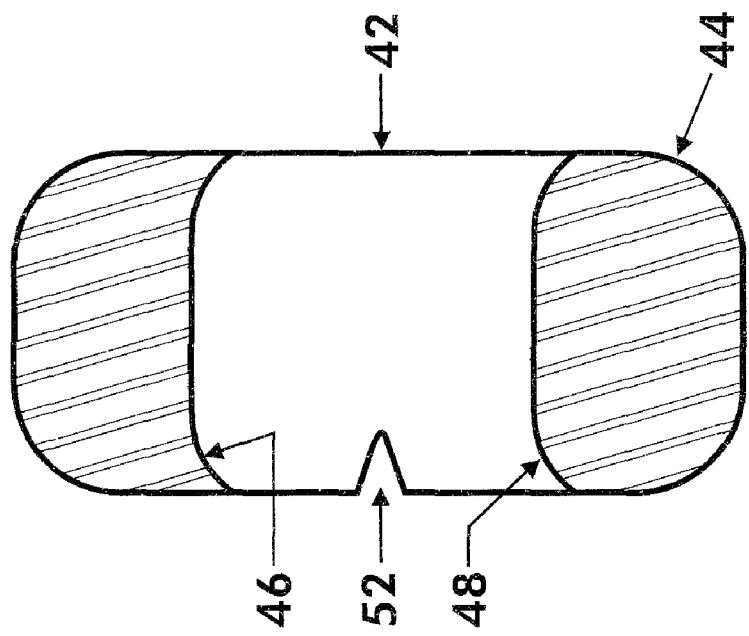
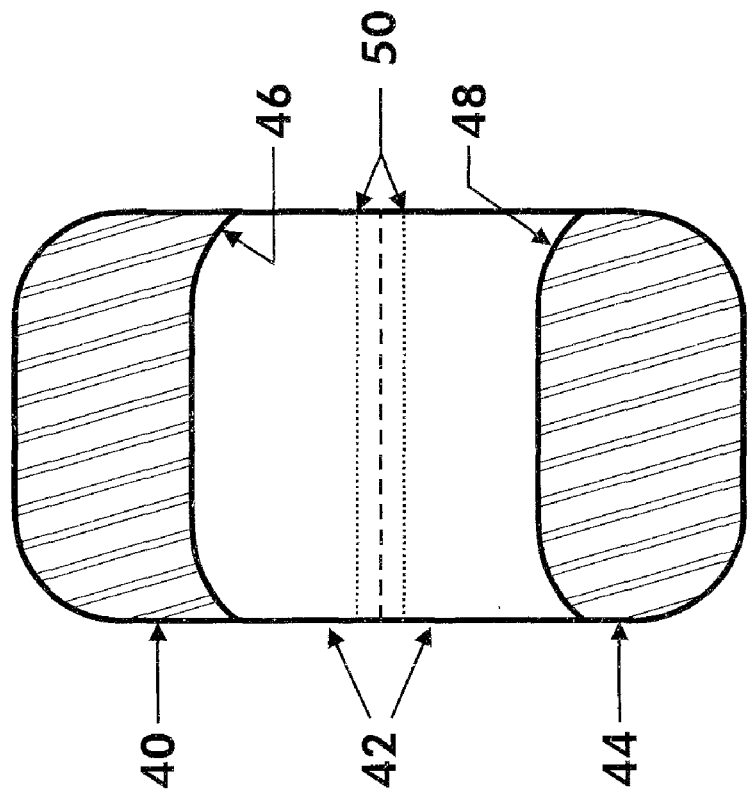

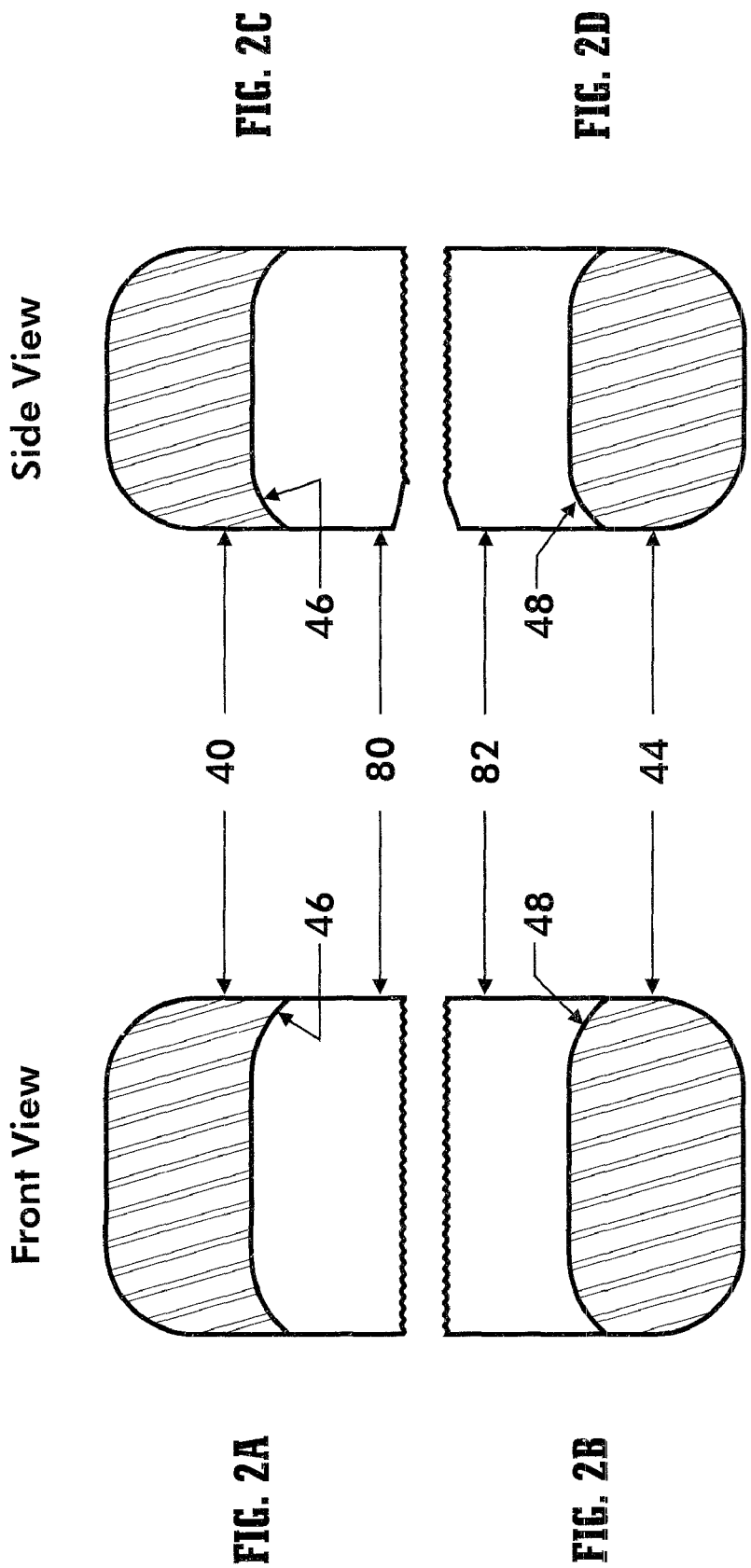

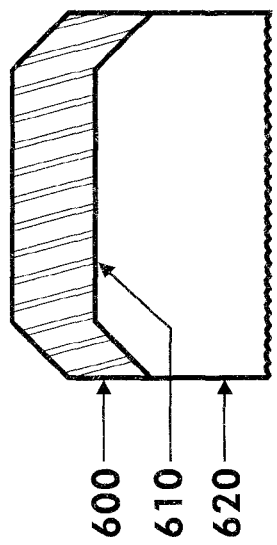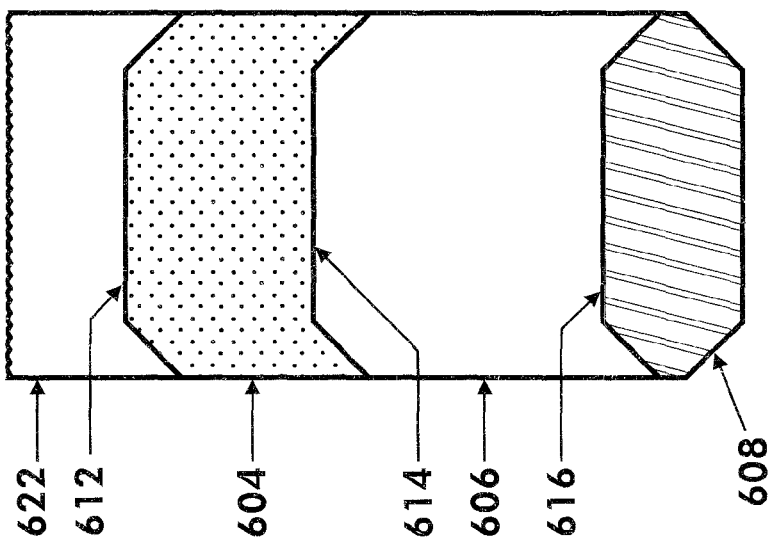
FIG. 6A
FIG. 6B

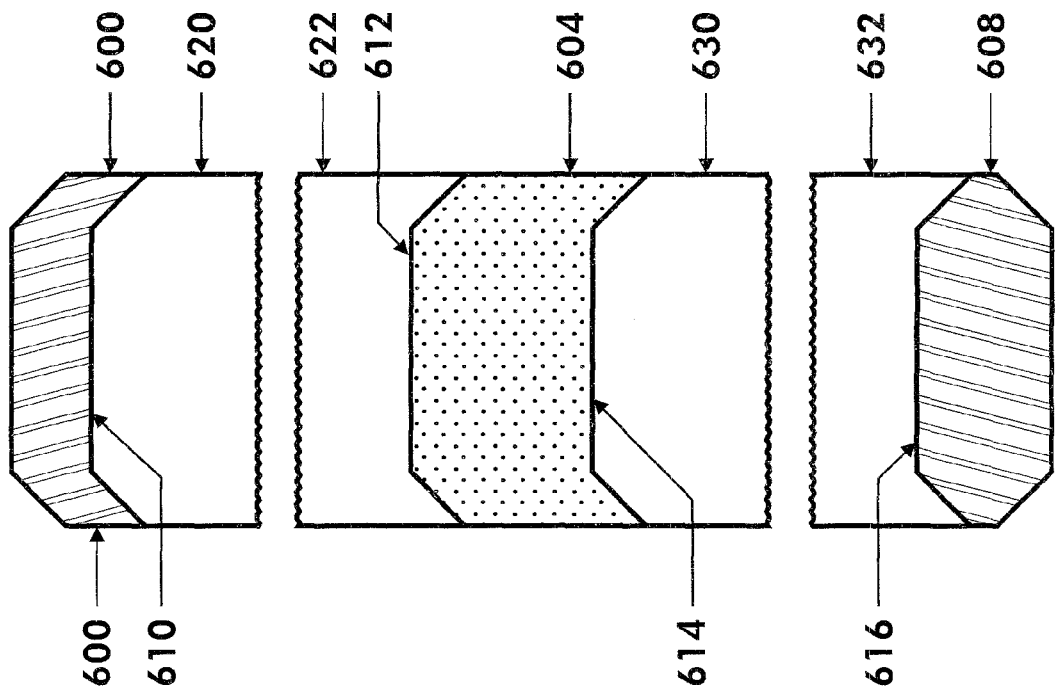

PHARMACEUTICAL TABLETS WITH HEIGHT GREATER THAN WIDTH

CROSS-REFERENCE TO RELATED APPLICATIONS

This is a continuation-in-part of U.S. patent application Ser. No. 11/569,343 filed Nov. 17, 2006, which is a Sect. 371 filing from PCT/US05/18633 filed May 23, 2005, which claims priority to U.S. Provisional Appl'n Ser. No. 60/573,042 filed May 21, 2004 and U.S. Provisional Appl'n Ser. No. 60/573,134 filed May 21, 2004, each of which is incorporated by reference in their entirety.

FIELD OF THE INVENTION

The invention provides non-homogeneous compressed pharmaceutical tablets that are taller than they are wide, said novel shape for immediate release tablets resulting in previously undisclosed advantages with regard to accurate breaking of the tablet so that breaking of the tablet may more easily produce predictable quantities of active ingredient(s) in the resulting broken portions.

BACKGROUND

Pharmaceutical tablets in divisible form containing an indentation known as a score have long been known and widely used. Problems with breaking scored tablets are well-known. These problems include loss of active drug and inaccurate division of the tablet, so that a tablet intended to be divided into two equal half-tablets often does not come close to that ideal.

Many drugs require dosage adjustments, such as warfarin, the scored tablets of which are frequently broken. These dosage adjustments through tablet breaking by patients have been determined to be imprecise. As the following discussion demonstrates, for many years experts have called upon the pharmaceutical industry to improve the quality of tablet breaking, yet such has not been optimized until the current invention.

In 1984, Stimpel et al. ("Stimpel"), described the relative accuracy of breaking of various tablets for treatment of cardiovascular problems. M. Stimpel et al., "Breaking Tablets in Half." *The Lancet* (1984): 1299. Even though breaking was performed by a sophisticated, dexterous person, Stimpel found that breaking was not accurate, and opined that real world use by patients would provide even more unsatisfactory results. Stimpel called upon the pharmaceutical industry to improve the accuracy of splitting tablets: "Clearly any assumption that halving a tablet will not lead to inaccurate doses is invalid. This potential source of inaccuracy could be even more significant in clinical situations (our study was done under ideal conditions) and the pharmaceutical industry should tackle it, either by improving divisibility (as already has been done for Lopressor and Logroton) or, even better, by marketing a wider range of unscored tablets to provide all the doses that might be indicated clinically."

Despite that finding and statement, and despite the issuance of various patents relating to optimizing a scoring pattern and/or tablet shape, Rodenhuis et al., (2004) noted that: "Improving the functioning of score lines may be a more practical approach than banning this dosage form" (emphasis added). N. Rodenhuis et al., "The rationale of scored tablets as dosage form." *European. J. of Pharmaceutical Sciences* 21 (2004):305-308 (hereafter "Rodenhuis"). Rodenhuis observed that European regulatory authorities started a policy to discourage scoring of tablets in 1998. This policy change, according to Rodenhuis, is likely related to "many recent reports of bad functioning score lines" where "many scored tablets are difficult to break," and that "many scored tablets show unsatisfactory mass uniformity of the subdivided halves." The authors then went on to describe useful aspects of scoring tablets. For a comprehensive review article on this topic, see van Santen, E., Barends, D. M. and Frijlink, H. W. "Breaking of scored tablets: a review." *European J. of Pharmaceutics and Biopharmaceutics* 53 (2002):139-145.

Some current studies that demonstrate the severity of the problem are described below: Peek et al., (2002), studied tablet splitting by "elderly patients" aged 50-79. Peek. B. T., Al-Achi, A., and Coombs, S. J. "Accuracy of Tablet Splitting by Elderly Patients." *The Journal of the American Medical Association* 288 No.4 (2002):139-145. Breaking scored tablets with mechanical tablet splitters without specific instruction led to highly unsatisfactory separating of the tablets. For example, warfarin 5 mg was on average split into 1.9 and 3.1 mg tablets. This potent anticoagulant has such a narrow therapeutic range that 2, 2.5, and 3 mg tablet doses are manufactured. Biron et al., (1999), demonstrated that warfarin 10 mg also often split to less than 4.25 or greater than 5.75 mg. Biron, C., Liczner, P., Hansel, S. and Schved, J. F., "Oral Anticoagulant Drugs; Do Not Cut Tablets in Quarters." *Thromb. Haemost.* 1201 (1999). In addition, they demonstrated that loss of mass due to crumbling or chipping from the breaking of the warfarin tablets was statistically significant. They also demonstrated that quartering of the tablets was grossly inaccurate.

McDevitt et al., (1998), found that 25 mg unscored hydrochlorothiazide tablets were manually split badly enough that 12.4% of the tablets deviated by more than 20% from ideal weight. McDevitt, J. T., Gurst, A. H. and Chen, Y. "Accuracy of Tablet Splitting." *Pharmacotherapy* 18 No.1 (1998):193-197. 77% of the test subjects stated that they would be willing to pay a premium for individually produced 12.5 mg tablets rather than split 25 mg unscored tablets.

Rosenberg et al., (2002), studied pharmacist-dispensed split tablets. Rosenberg, J. M., Nathan, J. P. and Plakogiannis, F. "Weight Variability of Pharmacist-Dispensed Split Tablets." *Journal of American Pharmaceutical Association* 42 No.2 (2002):200-205. They found that "tablet splitting resulted in an unacceptably high incidence of weight variation." They recommended that "standards should be developed to ensure uniformity of split tablets."

Teng et al., (2002), using a trained individual in a laboratory setting to split tablets, concluded that "the majority of the 11 drug products we tested, when assessed for their ability to be split into half-tablets of equal dose, failed a liberally interpreted USP (United States Pharmacopeia) uniformity test ... The practice of dividing tablets to save costs or to improve a dosage regimen ... is not recommended for patients using drugs with more substantial toxicity and steep dose-response efficacy curves." Teng, J., Song, C. K., Williams, R. L. and Polli, J. E. "Lack of Medication Dose Uniformity in Commonly Split Tablets." *Journal of American Pharmaceutical Association* 42 No. 2 (2002):195-199.

Rodenhuis reported that 31% of all tablets in one Netherlands study were subdivided before being swallowed. In the U.S., "managed care" insurance organizations may encourage splitting by patients of unscored tablets that may not even have symmetrical shapes. Many drug products in the US either are unscored tablets, or are provided as capsules despite being able to be produced as tablets.

The invention is directed to amelioration of the problems described above.

In addition, treatment with combination products is common in pharmaceuticals, meaning that one dosage form may contain more than one active ingredient. This means of treatment may in part be discussed as follows:

A relevant field to the invention is the field of combination drug therapy for systemic arterial hypertension ("hypertension"). Technically, combination therapy for hypertension involves the use of two or more drugs on a regular basis to treat a patient's hypertension. Generally, this term implies daily treatment with at least two drug products.

Combination therapy has long been used to treat hypertension. It is widely estimated that approximately half of all cases of hypertension cannot be treated to goal blood pressure with one drug at a maximally tolerated dosage. To aid in treatment, solid oral dosage forms have been produced that contain a plurality of active agents within one tablet or capsule. These dosage forms are known as "fixed-dose" combination products, because a patient or pharmacist has no means of separating one active agent from another. Sica, D., Drugs. 2002; 62 (3): "Rationale for Fixed-Dose Combinations in the Treatment of Hypertension," states that "a considerable legacy, dating to the 1950's, exists for fixed-dose combination therapies." Later in the same article, the author pinpoints a deficiency with the fixed-dose approach, which embodiments of the current invention largely correct: "A disadvantage to the use of fixed-dose combination is a lack of dose administration flexibility for its individual components, although it is uncommon for physicians to maximally exploit the dose administration flexibility inherent to the use of free combinations. With fixed-dose combination therapy, if conditional amounts of either drug are required for BP control, a separate prescription will be required. This increases complexity of the regimen and has the potential to negatively affect compliance. In addition, fixed-dose combination therapy may not provide adequate drug amounts to manage illnesses such as angina or congestive heart failure, which commonly co-exist with hypertension."

The invention provides a means to improve the above situation, by allowing flexibility of dosing within a combination dosage form.

The current invention describes a tablet shape adapted for separating one vertically disposed segment from another.

In the large field of immediate release pharmaceuticals, the relative dimensions of the tablet are novel. Commercially, the only product that as produced is taller than it is wide is Concerta®, which is a three-segment tablet, two of which segments are devoted to controlled release of the active drug, methylphenidate. Concerta® utilizes the OROS® system, which utilizes the taller-than-wide geometry as part of its controlled release characteristics. The manufacturer's directions for the use of Concerta® specify that the tablets should never be broken.

Except for Concerta®, tablets, including those involving layers vertically disposed one on the other, have been produced wider than they are tall.

A tablet press manufacturer, Korsch AG of Germany, has developed a tablet press that can produce tip to five vertically disposed layers. It has been utilized to produce taller-than-wide five-layer tablets having no active drugs therein and has also been used to manufacture Concerta®.

SUMMARY OF THE INVENTION

The invention is directed to a compressed pharmaceutical tablet that has two or more segments, has a top and a bottom, and has a height that exceeds the width of said tablet, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides.

A preferred embodiment of the compressed pharmaceutical tablet is one that comprises two or more segments disposed one above the other.

The invention contemplates immediate release pharmaceutical tablets or controlled release tablets, preferably containing a pharmacologically effective quantity of an active pharmaceutical ingredient, or drug, where the height of the tablet (vertical dimensions) exceeds its width (horizontally dimension); i.e., the tablet is taller than it is wide. The terms "vertical" and "horizontal" ("horizontal" is also referred to as "transverse") axis of the tablets of the invention are determined by and have the same orientation as that of the tablet die in which the tablet is compressed in a tablet press or other tabletting machine ("tablet press" herein), and the order of entry of granulations into the die.

Tablets of the invention are most preferably produced for commercial sale in a high-speed tabletting machine. Tablets are produced in a die of said tabletting machine. In such a machine, granulations enter the tablet die one on top of another, so that said granulations are said to be vertically disposed to each other. Layers and segments formed from vertically disposed granulations are considered to be vertically disposed, as well. The height ("tallness") of a tablet is measured as the vertical distance between the lowest part of the first granulation to enter the die to the highest part of the last granulation to enter the die (said first granulation forms the bottom layer and said last granulation forms the top layer).

The width is a horizontal (transverse) dimension. In determining the width, diagonal measurements are not taken through the horizontal aspect of the tablet if the tablet is substantially rectangular in transverse cross-section: if the perimeter of the horizontal aspect of the tablet were rectangular (and not square), then the width of the tablet would be the greater of the two perimeter measurements as is typically used to describe a rectangle, and not the diagonal that is calculated by the Pythagorean theorem and that uses said perimeter measurements to calculate said diagonal. Similarly, tablets with a substantially rectangular vertical cross-sectional configuration have a height that is measured as a perimeter and not a diagonal measurement. When a vertical or horizontal cross-sectional configuration is not substantially rectangular, which includes triangles, rhombi, and hexagons, the greatest dimension through said cross-section represents said height or width.

Many of the preferred tablets of the invention utilize segments that lack a pharmacologically effective dose of a drug to serve as a region for breaking if any accurate partial dose of drug found in the whole tablet is desired. By convention herein, the term "contains a drug," when used to refer to a granulation, layer, or segment of a tablet, said granulation, layer, or segment has within it a pharmacologically effective dose of a drug. The term "contain a drug" when used to refer to a plurality of granulations, layers or segments, such as two granulations or two segments, means that said granulations, layers, etc. have within them a pharmacologically effective dose of a drug. The term "contain a drug or drugs" when used to refer to a granulation, layer, or segment means that said granulation, layer or segment may contain either a single drug or a specific ratio of a plurality of drugs. When "contain a drug or drugs" is used to refer to a plurality of segments, layers, or granulations, that term means that the plurality of granulations, layers or segments may contain either a single drug or a specific ratio of a plurality of drugs.

A layer or segment, but not a granulation, is said to "lack a drug (or drugs)" if said layer or segment either contains none of said drug (or drugs) or contains a pharmacologically ineffective amount of said drug.

Parts of speech, such as "contain," "contains," "containing," and "lacking" in relation to the above two paragraphs also are terms of art with otherwise the same meanings to those described therein.

In preferred embodiments, but without limitation, the invention comprises compressed pharmaceutical tablets where one or more drugs are disposed in segments where:
  (a) said tablet includes two or more segments that contain the same drug or drugs in the same or different concentrations relative to the excipients found in said segments, and the tablet is not provided with another drug than is found in said segments; or
  (b) said tablet includes two or more segments, each segment of which contains a different drug or drugs; or
  (c) said tablet includes a first segment containing a drug or drugs; a second segment; and a third segment containing a drugs or drugs which are different from the drug or drugs in said first segment, said second segment being interposed between said first and said third segment (i.e., below one of said segments and above the other) and said second segment lacks said drug or drugs; or
  (d) said tablet includes a first segment containing a drug or drugs; a second segment; and a third segment containing the same drug as the drug in said first segment, said second segment being interposed between said first and said third segment, and said second segment lacking said drug or drugs.

In a more preferred embodiment, the tablets of the invention have at least two compositionally distinct segments, with a first segment containing an active drug or drugs in a pharmacologically effective amount and a second segment that:
  (a) contains the same drug at a lower concentration than the concentration of said drug in said first segment, or contains the same ratio of the drugs in said segment; or
  (b) lacks said drug or drugs present in said first segment and the tablet also has a third segment containing the same drug that is present in said first segment; or
  (c) lacks said drug or drugs in said first segment, and said tablet also has a third segment containing a drug or drugs different from any in said first segment, wherein said first and third segments are chemically and physically compatible; or
  (d) has a different drug than the drug in said first segment and also includes a third segment containing the same drug that is present in said first segment.

A further preferred embodiment may optionally contain guides for tablet breaking, such as a score, indicia, printed indicia, a perforation, contrasting color segments, and the like on or in the side of the tablet, with a score preferably being substantially horizontal to allow tablet breaking only through one segment or an interface between segments. A side of a tablet is an external part of said tablet that has a vertical part that is substantially parallel to the theoretical vertical axis of the tablet; a side is in contact with the inner wall or face of the tablet die in which said tablet is compressed.

Taller-than-wide tablets of the invention are shaped to be more easily broken through the tablet's theoretical vertical axis (i.e., in a horizontal direction) than are conventional, currently manufactured tablets having a "wider than tall" configuration. Many preferred uses of tablets of the invention are to break through an interposed segment of the tablet lacking a pharmacologically effective dose of a drug without breaking through a segment above or below said interposed segment.

It is a primary object of the invention to provide an immediate release or controlled release pharmaceutical tablet that may be easily broken to provide a partial dose of a drug or drugs that is contained in said tablet.

It is also an object of the invention to provide a pharmaceutical tablet having three segments, one of which is an interposed segment which is adapted to be broken through in such a manner as to keep the segments between which it is interposed and that contain pharmacologically effective quantities of a drug or drugs substantially intact if said tablet is broken through said interposed segment.

These and other objects of the invention will become apparent from the present application.

BRIEF DESCRIPTION OF THE SEVERAL VIEWS OF THE DRAWINGS

FIG. 1A is a cross-section of a taller than wide tablet viewed from the side of the tablet having a score; FIG. 1B is a cross-section of the tablet of FIG. 1A looking at the side of the tablet where the score ends;

FIGS. 2A-2D are views of FIG. 1A and FIG. 1B respectively when the tablets have been broken through the score.

FIGS. 6A-6B are views of FIG. 5 when the tablet has been broken through one segment.

FIGS. 7A-7C are views of FIG. 5 when the tablet has effectively been broken through two segments in two steps, first by breaking the tablet and then by breaking the tablette of FIG. 6B.

DETAILED DESCRIPTION OF THE INVENTION

Figure 3:
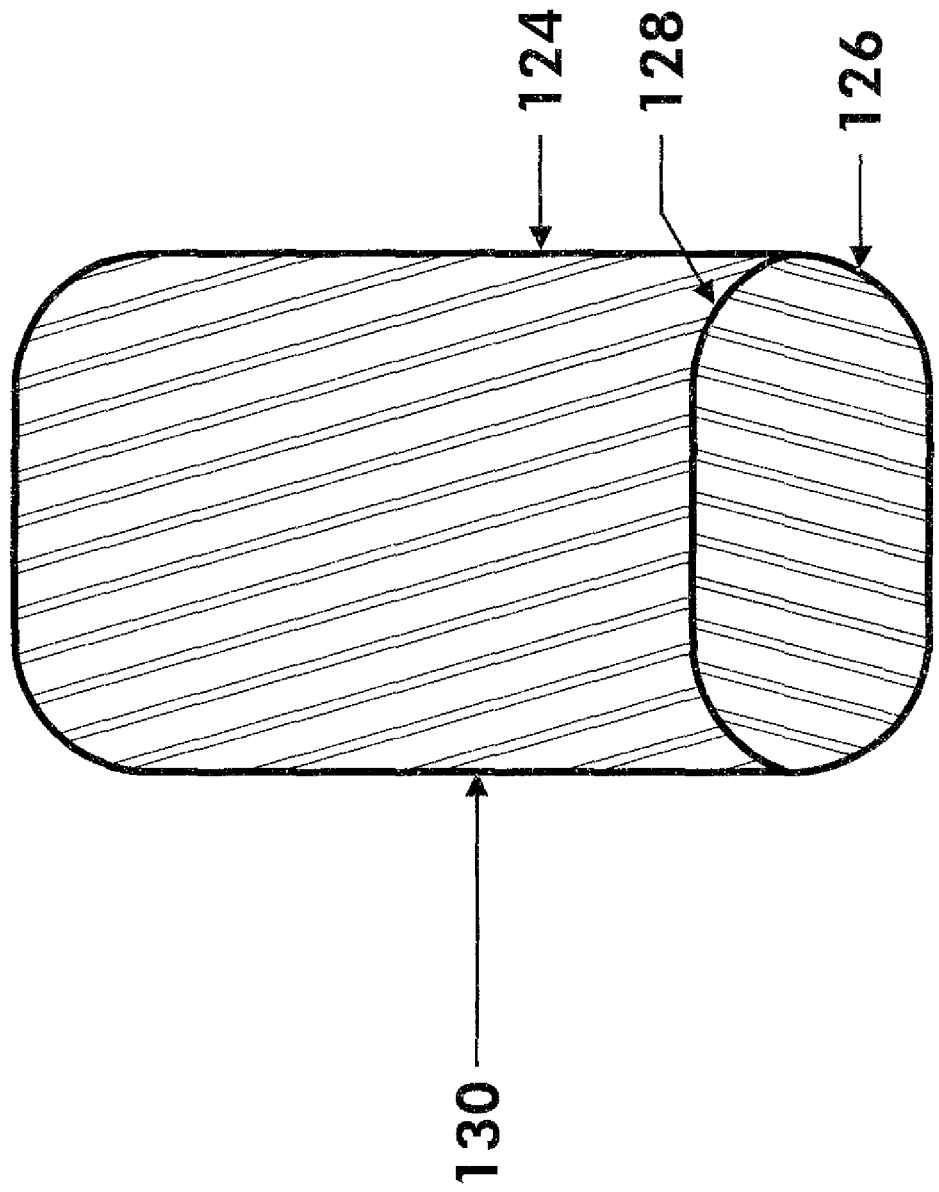
FIG. 3 is a cross-section of a taller than wide tablet having two segments, one of which is about three-quarters of the length of the tablet.

Tablets of the invention are preferably those compressed in a tablet press. For commercial use, a high-speed three (3)- or five (5)-station press produced by Korsch AG may be utilized. Remington's Pharmaceutical Sciences 20th Ed., Mack Publishing Co., Easton, Pa. (2000), Chapter 45, which is incorporated by reference, describes the various techniques utilized in making compressed tablets. The tablets of the invention are primarily intended for oral administration but they may also be used for other applications. Tablets of the invention are not formed using a cement, glue, adhesive, or the like, and call be coated or uncoated.

The tablets of the invention can comprise at least two compositionally different segments.

A segment represents the entirety of a contiguous, substantially homogeneous part of a tablet or tablette (see below) of the invention. If two or more consecutive granulations entering the die are substantially identical, then when compressed, they will form one segment. Such a segment is a sub-type of segment that may be referred to specifically as a compound segment. If, however, two substantially non-identical granulations (such as those containing different active drugs, the same active drugs in different ratios, different excipients or different ratios of similar excipients, or different salts of the same active drug) were compressed onto each other, they would comprise two segments. Granulations comprising the same active drug in the same concentration relative to excipients but with dissimilar excipients would comprise two segments if one granulation were compressed onto another.

A layer is produced by introducing an amount of an individual granulation into a tablet die to fill at least a part of the die. A layer is considered to be present whether it is the form of all un-tamped, tamped or fully compressed granulation.

In many of the most preferred tablets of the invention, a layer (and the granulation from which it is derived) will not need to be placed on top of or below (e.g., adjoining, or contiguous with) a substantially identical layer (or granulation). In such a case, one layer will give rise to the sub-type of segment that is a simple segment. The use of the term "segment" allows a segment to be simple or compound. Because the tablets of the invention have been adapted to be broken if and when desired, it has proven useful to develop a term for the major fragments of said breaking. The inventors use the term "tablette" in this regard. An example of tablette formation is as follows. A standard single-scored, mono-layer, homogeneous pharmaceutical tablet is broken.

Said breaking produces two major fragments, each of which is called a tablette, generally plus some chips and crumbling which are preferably minor in amount. In the segmented, layered tablets of the invention, to utilize the invention properly may make it advantageous to place a score transversely into a segment, such as an inner segment, as may be done with an instrument such as a file. Successfully breaking said tablet through said score will result in two tablettes, representing the two major fragments of the tablet and not including smaller fragments such as crumbs or chips. The accompanying diagrams help clarify the relationship of tablets to tablettes.

The terms "active agent," "drug," "active drug," "active pharmaceutical agent," and "pharmacologically active agent" are interchangeable and include, without limitation, prescription and non-prescription pharmaceutical compounds, as well as pharmacologically effective doses of vitamins cofactors, and the like. Substances such as foodstuffs, vitamins in "recommended daily allow" quantities, and the like are not considered to be "drugs" herein.

The term "undetectable amount" means that when using conventional analytical techniques such as high performance liquid chromatography (HPLC), nuclear magnetic resonance imaging (NMRI), and the like, the presence of an active compound can not be identified. The term "pharmacologically ineffective amount" means an amount of a drug or drugs that has or have no measurable pharmacological effect. Due to the conditions under which high speed automated tabletting equipment are operated, mixing of different granulations may occur during tablet formation which may cause material such as drug substance present in one granulation to appear in a layer or segment where it was not intended to be placed.

The term "relatively inactive segment" refers to a segment that either contains an undetectable amount of any drug or contains a diminished concentration of any pharmacologically effective drug or drugs contained in another segment or segments.

The terminology used herein is for the purpose of providing a general understanding and is not intended to be limiting.

As an example of a method of manufacture of a preferred tablet of the invention, first, a granulation containing a pharmacologically effective dose of a drug enters the die and is tamped. Second, a granulation lacking a drug (an "inactive granulation") enters the die and is tamped. Optionally, another inactive granulation lacking active drug also enters the die and is tamped. The inactive granulation(s) creates a part of the tablet that can be identified and broken through so that a part of the drug containing a significant concentration of drug is not broken through. Last, a second granulation containing a pharmacologically effective quantity of a drug enters the die, is optionally tamped, and then final compression to form a compressed tablet occurs. While one or all segments may individually have a width greater than height, the tablet as a whole has a height that exceeds its width.

Subsequent to tablet formation, optionally a score may be placed in the side of said tablet, preferably transversely. Alternatively, after tablet formation, a printed line or other forms of indicia such as dotted lines, symbols or perforations may be placed on or in the surface of the tablet, all of which serve the purpose of allowing identification of said tablet's desired breaking region from the standpoint of effecting accurate separation of the parts of a tablet containing isolated doses of drug. Other means of aiding identification of a region of potentially desired tablet breaking may be utilized such as the use of contrasting colors in different segments.

Suitable dimensions for tablets according to the invention are: height: 6 to 24 mm; preferably 10 to 18 mm and more preferably from 10 to 14 mm; width (at the widest dimension of the horizontal axis): 2 to 16 mm: preferably 3 to 10 mm and more preferably 4 to 8 mm. Without limitation, the dimensions of the tablet may be optimal if the ratio of the height to the width is between about 1.5:1 to about 3:1.

Numerous other structures may be created, some of which are further delineated below. Various advantages in the treatment of human patients and other animals in need are created by tablets of the shape described.

Tablets of the invention are most preferably formed in a high-speed tablet press. In a typical manufacturing procedure, two or more different granulations are separately fed into a die, utilizing different filling stations. Wet granulations are often preferred to limit transfer of material from one granulation to another. Direct compression of powder is also a preferred manufacturing technique.

Full entry of a granulation at a filling station produces a layer. Tablets of the invention have a layered structure. It may be relevant to add two consecutive substantially identical inactive granulations to form two identical, contiguous layers. After compression, the part of the tablet formed by said two identical granulations is referred to as a segment. The type of segment so formed is called a compound segment. There also may, in the case in which a large quantity of an active ingredient is desired to be in one segment, be cause to have two substantially identical granulations containing said active ingredient to enter at two consecutive filling stations, thus producing, after final compression to form a tablet, a compound segment that contains active drug. The more common case is that in which a first granulation enters the die not on top of a substantially identical granulation (layer), forms a layer, and a substantially non-identical (i.e., different) granulation next enters said die, so that said first granulation forms a layer that is not contiguous with a substantially identical layer. Said first granulation forms a layer that is considered to be a simple segment in the compressed tablet.

The benefits of the invention include the utilization preferably of inactive granulations and less preferably, segments with diminished concentration of a drug relative to another segment. Optimally, the tablet is provided with a means of identifying an optimal breaking region and of identifying one tablette from another after tablet breaking, an important benefit if the tablettes contain different types or quantities of a drug or drugs.

Because of the novelty of the tablets, it is necessary to describe the top, bottom, sides, etc. of the tablet. It has been found best to describe the tablet with regard to such terms based on said tablet's formation and location in the die in which said tablet is formed.

As used herein, such terms as "horizontal" ("transverse") and "vertical" when used in relation to a tablet, are based on the spatial orientation of the tablet as, and after, it is produced in a die, but before removal or ejection from the die. Current methods of manufacture produce tablets with one granulation entering the die on top of another, so that tablets of the invention produced in such a manner comprise one or more top (outer) segments, one or more bottom (outer) segments, and optionally one or more middle (inner) segments. A segment that is not a top or bottom (collectively, "outer") segment is considered to be an inner segment, even though of course an inner segment has an external aspect. The number of inner segments is not limited.

The bottom segment of a tablet contains the first granulation to enter the die. The top segment of a tablet contains the last granulation to enter the die. A "side" of the tablet refers to that external part of said tablet in contact with the internal vertical face or aspect of the tablet die in which said tablet is produced. Typically, sides of the tablets of the invention are vertically oriented, in contrast to the tops and bottoms of the invention. In the case of cupping and beveling of the top of the tablet, which may from time to time be extensive, the tablet's side is considered to also include the external part of the tablet that was in contact with the internal vertical face or aspect of the tablet die before a top punch formed said cupping, beveling, or the like.

If separate granulations were to be sequentially placed in a die horizontally (side-to-side) and not vertically as is currently the practice, then the tablets so produced would be within the scope of the present invention as the same product would be produced. When the tablet of FIG. 1, for example, is laid on a flat table, it will tend to lie lengthwise at right angles to the manner in which it is formed in the die (i.e., its longest axis would lie horizontally in relation to the tabletop), so that if the three segments were all different colors, then the segments would appear to be arranged not vertically (one on top of the other), but rather horizontally (side-to-side). For consistency of terminology, such segments nonetheless are considered herein to be disposed vertically on top of each other, because of the manner in which they were created.

The major advantage of the invention is that it optimizes optional tablet breaking. When force is applied to break a tablet, breaking of the tablet tends to more easily produce predictable quantities of active ingredient(s) in tablettes than "wider than tall" tablets with segments containing the same quantities of drugs. The tablet may be broken according to the invention either by applying force such as a cutting edge directly to the region to be broken through, or to outer segments, potentially in either case breaking through an inner segment.

Examples of specific embodiments of the invention are best described with reference to the drawings. Shaded areas represent segments derived from active granulations, i.e., those which contain a drug; clear (plain) areas represent segments derived from inactive granulations, i.e., those formulated with no active drug.

The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet.

"Front views" refer to a cross-sectional view of a tablet that has a theoretical geometric plane passed through the tablet relative to a side which is arbitrarily designated as the front, Figures labeled as "side view," which also have a corresponding "front view" are taken as a cross-section through the whole tablet from the right side of a front view i.e., a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view. That plane is located half-way between the front and back surfaces of said tablet. The side views of FIGS. 1a-1b and 2a-2b are taken from a vertically-oriented plane that passes through the midpoint of the longer transverse dimension (i.e., the width), and thus are located at and perpendicular to the mid-point of the front view. Drawings are of tablets that have a rectangular but not square horizontal cross-section at the vertical mid-point of the tablet.

Segments containing pharmacologically active amounts of a drug or drugs are shown crosshatched; pharmacologically ineffective segments are shown plain (clear, without crosshatching or stippling). The upper part of each figure corresponds to the upper part of a tablet, all of which are depicted as they are situated within a die after final compression and before ejection from the die. For consistency, tablettes are depicted in the same orientation as the tablets from which they are formed, although tablettes are created after tablet ejection from the die. Dotted lines in the tablets depicted in the Figures may represent printed marks or other indicia, or scores that are present on or in the surface of the tablet and, if they represent a score, said score does not extend deeply enough into the tablet to appear in the cross-sectional front view. The transverse dotted lines reflecting scores shown in the Figures imply no intention to limit the depth of any scores of the tablets of the invention. Horizontal clotted lines on the front views that represent the surface scores are schematic, and do not necessarily represent the full vertical extent of a score, printed mark, or the like.

Tablettes are depicted with broken surfaces as indicated by a fine saw-tooth pattern. Such saw-tooth depiction is schematic and not intended to represent the actual pattern of breaking of a tablet (or tablette), which often leads to irregular edges even if said tablet is broken through a score.

Grasping and breaking said tablet is easier with the current, taller-than-wider design than would be thee ease under layered (segmented) tablets known to the art, in which breaking a tablet through one segment only, if feasible, would require "filleting" the tablet through its longest axis.

FIGs. 1A and 1B depict a tablet with compositionally substantially identical upper segment 40 and lower segment 44. Inner segment 42 contains trace amounts of the drug that is present in a therapeutically effective quantity in each of segments 40 and 44. Interfaces 46 and 48 represent regions in which the upper part of segment 42 and the lower part of segment 42 respectively adjoin upper segment 40 and lower segment 44. The curved interfaces result from the profile of the upper tablet punch which is curved. Score 52 is depicted in FIG. 1B. Dotted line 50 in FIG. 1A is a reflection of score 52 on the surface of the tablet (not shown), that does not penetrate half-way through the shorter transverse axis of the tablet.

FIGS. 2A-2D depict tablettes formed from breaking the tablet of FIGs. 1A and 1B through score 52. Inner segment 42 of FIG. 1A no longer exists as an intact segment. The upper tablette of FIGS. 2A and 2C contains segment 80 that adjoins intact upper segment 40 and the lower tablette contains segment 82 and intact segment 44.

Breaking the tablet of FIGS. 1A and 1B through the score placed in segment 42 is clearly easier than breaking the tablet through its vertical dimension, which is currently the practice with scored layered (segmented) tablets. The fact that no break is made in the parts of the tablet where the active drug has been placed provides for exceptionally accurate breaking relative to the active drug or drugs contained in the tablet.

Figure 4A:
FIGS. 4A-4B are views of FIG. 3 when the tablet has been broken at the approximate mid-point of the tablet.
Figure 4B:
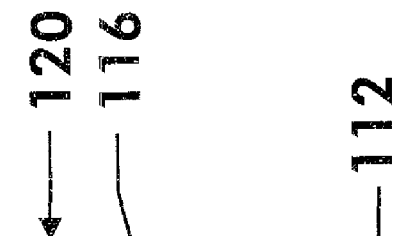

FIG. 3 demonstrates a two-segment tablet, each segment formed from a granulation containing a pharmacologically effective amount of medication. Upper (outer) segment 124 is larger than lower (outer) segment 126. Interface 128 indicates a region at which said segments are contiguous. A printed mark on the outer surface of the tablet (not shown) indicates a desired breaking point, as indicated by the location of arrow 130 that reflects the position of said surface printed mark. The two segments also have different color, however, further allowing identification of which part of the tablet contains which segment FIGS. 4A and 4B depict the two tablettes formed by breaking the tablet of FIG. 3. The tablette of FIG. 4A consists of segment 118, which represents the bulk of segment 124 of FIG. 3. The tablette depicted in FIG. 4B contains segment 112 in an intact form and segment 120, which represents a less than half-portion of segment 124 of FIG. 3. Interface 116 indicates a region at which said segments are contiguous. The curved face is due to the profile of the tablet punch.

Figure 5:
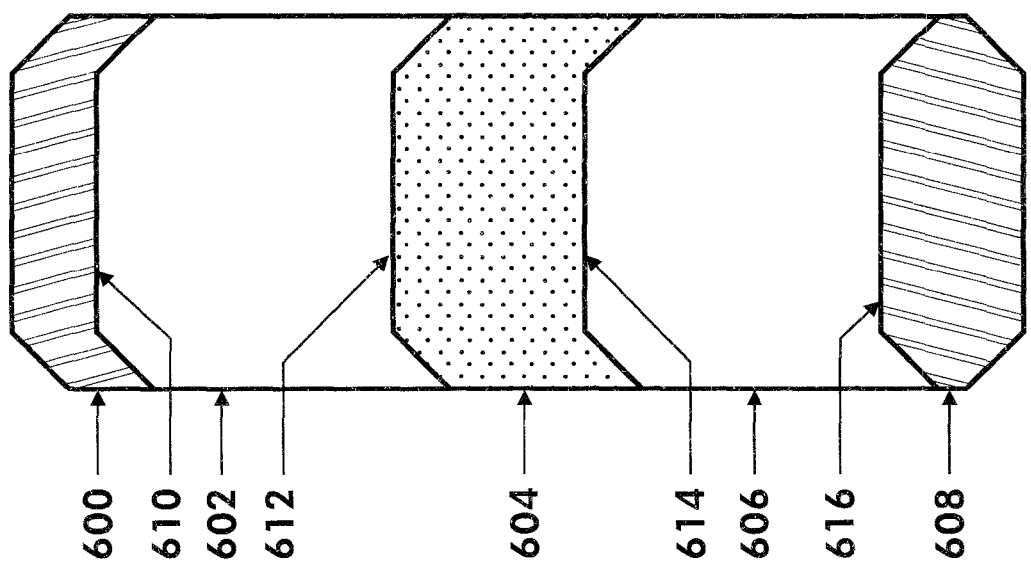
FIG. 5 is a cross-section of a taller than wide tablet having five segments.

FIG. 5 illustrates a tablet more elongated than those previously demonstrated. Said tablet is adapted, even more than the others, for ease of breaking through one segment. Upper segment 600 is provided with a therapeutic quantity of a drug; stippled inner segment 604 is provided with a therapeutic quantity of a different drug; and, lower segment 608 is provided with a therapeutic quantity of a drug different from that found in a therapeutic quantity in segments 600 and 604. Clear (plain) inner segments 602 and 606 contain pharmacologically ineffective amounts of each of the three drugs found in the tablet. Interfaces 610, 612, 614, and 616 represent the regions at which two contiguous segments adjoin. The tablet of FIG. 5 is provided with a different color for each segment. Even though there is no surface scoring or indicia, the color scheme is such that a person's attention may be directed to apply force to break the tablet through segment 602 to create the tablettes depicted in FIGS. 6A and 6B. FIG. 6A depicts the smaller tablette created by breaking the tablet of FIG. 5 through segment 602 in a transverse fashion. Segment 620 has been created by said breaking, and segment 602 of FIG. 5 no longer exists as an intact segment. FIG. 6B depicts the larger tablette created by said breaking of the tablet of FIG. 5. New upper segment 622 has been created.

FIGS. 7A-C depict three tablettes created by the subsequent breaking of the tablette of FIG. 6B. New segment 630 and segment 632 have been created and segment 606 no longer exists as an intact segment.

Figure 8:
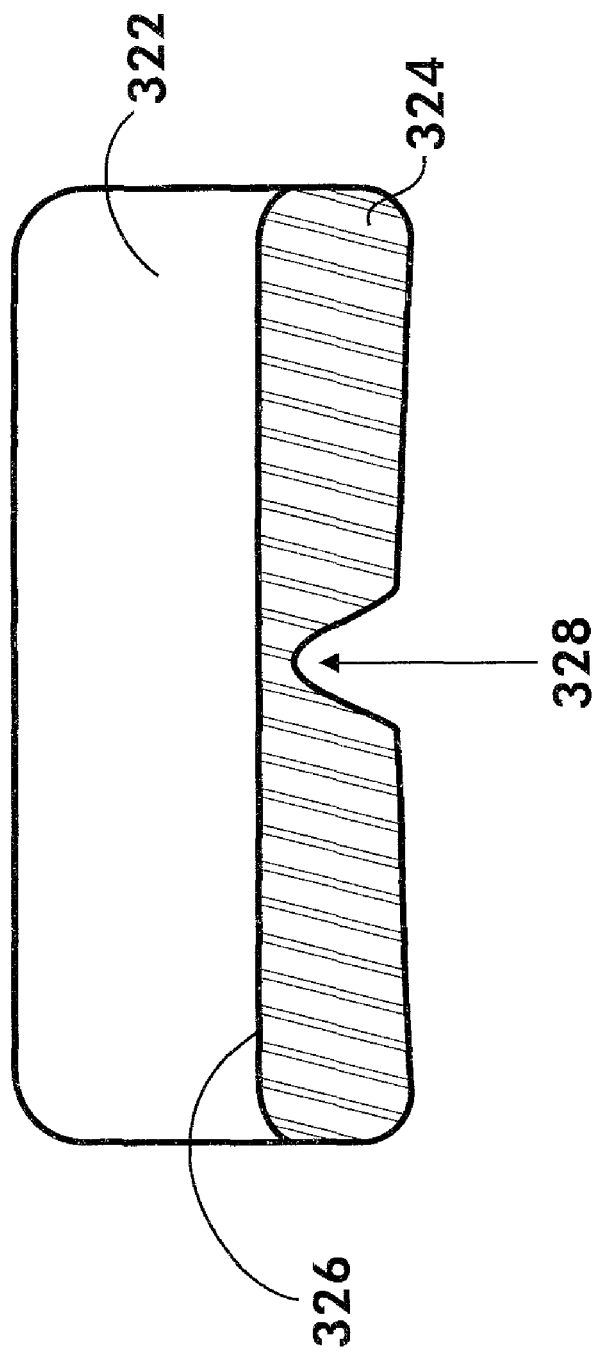
FIG. 8 is a cross-section of a tablet that is wider than it is tall and that has two segments.

FIG. 8 depicts a traditional two-segment tablet. In this tablet, lower (bottom) segment 324 contains a drug different from that contained in upper (top) part 322. Score 328 indents segment 324. Interface 326 is present at the region at which segments 322 and 324 meet. The tablet of FIG. 8 is not a tablet of the invention. It depicts a schematic of a tablet of the prior art of bilayer tablets. One may readily appreciate the difficulty inherent in attempting to break a tablet such as the tablet of FIG. 8 horizontally, through one segment only, or, analogously, a tablet similar to that of FIG. 8 but that in addition was provided with, say, a segment below that of segment 324.

Benefits of the invention are not limited to tablets of any specific number of active ingredients. All segments containing an active ingredient may contain the same drug, or segments may contain different drugs.

In order to fully realize the benefits of the inventions, a score may be placed into a segment (or interface between segments) of the tablet. This score may be formed in an inner segment with a file in a substantially horizontal manner, so that breaking the tablet through said score could lead to breaking through the inner segment while leaving the outer segments intact.

In addition, similar means of marking tablets may be followed such as by causing an edible ink to be placed on the tablets, thus delineating a desired region of the tablet, such as its middle segment. Such application is well known in the art. Other means of applying indicia are contemplated as within the scope of the invention.

DESCRIPTION OF MANUFACTURING PREFERRED EMBODIMENTS

A "taller than wide" tablet is made which has three segments, each with an active top or upper segment and an active lower or bottom segment separated by a substantially inactive middle segment. A Stokes 27-station tri-layer rotary tablet press is used. All formulations are directly compressible powder blends. The blending both of the amlodipine formulation and the benazepril formulation are performed in a Patterson-Kelly "V" blender. The middle segment consists of 194 mg of Nu-Tab® and requires no blending. The tablets are compressed using 0.131 inch by 0.3222 inch oval, concave tablet punches to a hardness of 35 kiloponds. The bottom segment is introduced first into the die. The tablet weight is 310 mg. Tablets so made are 8 mm tall; the inactive middle segment varies from 5-6 mm in height and a width of 4 mm. Weights in mg of the granulation comprising each segment are as follow:

| Bottom Segment | Mg. |
| --- | --- |
| Dibasic calcium phosphate anhydrous | 51.13 |
| Amlodipine besylate | 7.15 |
| Sodium starch glycolate (Explotab ®) | 2.48 |
| Magnesium stearate | 0.93 |
| FD&C Blue #1 Aluminum Lake | 0.31 |
| Total | 62.00 |

Manufacturing Instructions

1. Weigh each ingredient.
2. Screen each ingredient.
3. Triturate the color with the major diluent in geometric proportions using a suitable mixer.
4. Add the remaining ingredients except the lubricants to the color mixer from Step #3 and mix for desired time.
5. Add the lubricant to the blend from Step #4 and mix for desired time.

6. Add the blend to a suitable press fitted with the desired tooling and compress into tablets.

| Middle Segment | Mg. |
|---|---|
| Nu-Tab ® (compressible sugar 30/35 N.F.) | 194.00 |

| Top Segment | Mg. |
|---|---|
| Lactose 310 monohydrate | 42.03 |
| Benazepril HCl | 9.00 |
| Crospovidone | 2.16 |
| Magnesium stearate | 0.54 |
| FD&C Red #40 Aluminum Lake | 0.27 |
| Total | 54.00 |

Manufacturing Instructions

1. Weigh each ingredient.
2. Screen each ingredient.
3. Triturate the color with the major diluent in geometric proportions using a suitable mixer.
4. Add the remaining ingredients, except the lubricant, to the color mixer from Step #3 and mix for desired time.
5. Add the lubricant to the blend from Step #4 and mix for desired time.
6. Add the blend to a suitable press fitted with the desired tooling and compress into tablets.

Tabletting Instructions

1. Place the powder for active layer in hopper #1.
2. Place the powder for placebo layer in hopper #2.
3. Place the powder for active layer in hopper #3.
4. Compress layer #1 tablets to desired weight (tablets for layer #1 should form a soft compact).
5. Compress layer #1 & layer #2 tablets to desired combined weight of layer #1 and layer #2 weight (tablets should form a soft compact).
6. Compress the tri-layer tablet to the desired total tablet weight (layer #1 weight+layer #2 weight+layer #3 weight). Tablet should be at desired hardness.

A similar tablet of the invention is separately produced using the same top and bottom segments as the above, but using the following ingredients instead of Nu-Tab® for the middle segment. The following are blended using a Patterson-Kelly "V" blender.

| Ingredients for middle segment: | Mg. |
|---|---|
| Dibasic calcium phosphate anhydrous | 158.59 |
| Magnesium stearate | 2.79 |
| PVP K-30 | 2.62 |
| Total | 164.00 |

Manufacturing Instructions

1. Weigh each ingredient.
2. Screen each ingredient.
3. Place all of the ingredients, except the lubricant, into a suitable mixer and mix for desired time.
4. Add the lubricant to the blend from Step #3 and mix for desired time.
5. Add the blend to a suitable press fitted with the desired tooling and compress into tablets.

The tablets were compressed using oval 0.131 inch by 0.3222 inch, concave tablet punches to a hardness of 35 kiloponds. The bottom segment was introduced first into the die. The tablet weight was 280 mg. Tablets with said middle segment were 6 mm high, and the inactive middle segment was 3.5-4 mm high.

Tabletting Instructions

1. Place the powder for active layer in hopper #1.
2. Place the powder for placebo layer in hopper #2.
3. Place the powder for active layer in hopper #3.
4. Compress layer #1 tablets to desired weight (tablets for layer #1 should form a soft compact).
5. Compress layer #1 & layer #2 tablets to desired combined weight of layer #1 and layer #2 weight (tablets should form a soft compact).
6. Compress the tri-layer tablet to the desired total tablet weight (layer #1 weight+layer #2 weight+layer #3 weight). Tablet should be at desired hardness.

In a similar way, other taller than wide tablets can be made on a tablet press, such as the Korsch TRP900, which can produce taller tablets due to its design for deep filling cams which allow for deeper fills and greater distances between the upper and lower compression tools.

To make an oval 0.131 inch by 0.3222 inch, concave tablet that is 12 mm tall oil the Korsch TRP900 the formulator would have to increase the weight of the inactive Nu-Tab® middle segment to about 323 mg. Similarly to have a finished tablet height of 14 mm the tablet would be formulated with a middle segment weighing about 388 mg. If desired, one could use the second example for a middle layer, i.e., the dibasic calcium phosphate (DCP) formulation. In such a case making an oval 0.131 inch by 0.3222 inch, concave tablet that is 12 mm tall on the Korsch TRP900 the formulator would have to increase the weight of the inactive DCP middle segment to about 410 mg. Similarly, to have a finished tablet height of 14 mm the tablet would be formulated with a middle segment weighing about 492 mg.

The invention also includes the method of administering one or more drugs via the dosage forms such as tablets and tablettes of the invention to a patient, mammal, or other animal in need of pharmaceuticals for the prevention or treatment of an illness, maintenance of good health, retarding of aging, or other purpose. Included are methods of treating a patient with only one drug from a combination products such as with a novel tablette of the invention, enabling downward dose adjustment for a variety of reasons, or, in a similar vein, a patient may be treated with one whole tablet containing a plurality of active drugs and in addition receive only one drug from a similar tablet, thus enabling upward dose adjustment.

Combination products that can benefit from the invention, in which one drug is in an outer active segment and a second and different drug is in the other outer active segment, and an inactive middle segment as in embodiments such as was described above, include those containing the following pairs of drugs: amlodipine and either benazepril, chlorthalidone, or atorvastatin; benazepril and hydrochlorothiazide; olmesartan and hydrochlorothiazide; and many others, including the majority of the currently-produced combination products. Also included is the method of treating a patient with a precise partial dose of medication from a whole tablet, which may be a half or quarter of the whole dose, but may usefully be a different fraction. Warfarin especially may usefully be produced and dosed according to the invention with separable segments of the tablet that may but need not be halves, quarters, etc. L-thyroxine and digoxin are other examples that could so benefit, along with warfarin.

The following give possible clinical situations in which the tablets of the invention could provide important benefits.

1. A currently marketed product in the United States is Caduet®, which contains the active ingredients atorvastatin calcium (atorvastatin) and amlodipine besylate (amlodipine) which are largely homogeneously interdispersed in an unscored tablet. The product is indicated to treat both hyperlipidemia (atorvastatin) and hypertension (amlodipine). A patient ingesting this tablet daily may then undergo a blood test and be diagnosed as having liver dysfunction as manifested by elevation of an enzyme's concentration in the blood. The physician may then recommend cessation, possibly temporary, of atorvastatin, which is stated by the manufacturer to be a possible cause of liver dysfunction. A patient receiving Caduet, however, would have to thus also discontinue amlodipine, which is not in this example desired by the physician. A tablet of the invention in which atorvastatin and amlodipine were segregated in different outer active segments, separated by a middle segment of adequate dimensions, would be a clear advance over the current Caduet® formulation, because such a tablet would allow a patient to promptly continue ingesting amlodipine while stopping ingestion of atorvastatin, without having to go to a pharmacy and fill a new prescription for a tablet containing only amlodipine as the active ingredient, while having previously had the convenience of having both drugs combined in a single dosage form. The above embodiment of the invention represents an improvement over the current Caduet® dosage form.

Another clinical situation in which the invention is superior to Caduet® is one in which a patient receiving amlodipine 5 mg once daily and atorvastatin 20 mg once daily is advised by a physician to increase the daily amlodipine close to 10 mg once daily. A patient in possession of adequate tablets of the invention, with the active drugs segregated in a three-segment tablet, would be able to promptly increase the amlodipine dose by taking a whole tablet of the invention once daily, plus a tablette containing 5 mg of amlodipine, produced by breaking a second whole tablet of the invention.

Another clinical situation in which the invention is superior to Caduet® involves the case in which a physician wishes a patient to ingest atorvastatin 20 mg each morning and amlodipine 2.5 mg twice daily. The invention provides for amlodipine to be separated from atorvastatin and then broken precisely in half. The invention thus allows the patient the advantage of one tablet, whereas to accomplish this currently in the United States would require one 20 mg Lipitor® (atorvastatin) tablet and two Norvasc® (amlodipine) 2.5 mg tablets.

2. The combination of amlodipine besylate and benazepril hydrochloride (benazepril) is marketed in the United States cinder the brand name of Lotrel®. This product is a capsule that is routinely ingested whole. An embodiment of the invention provides a whole tablet containing one outer segment containing amlodipine as the only active drug and the other outer segment containing benazepril as the only outer drug. If desired, either outer layer may be formed into more than one segment, as in FIG. 1a. As in example 1 above regarding Caduet®, the middle segment is inactive and may be broken through to create two tablettes, each comprising a whole amount of each outer active segment plus approximately half of the amount of the middle inactive segment. If a patient were to develop a need for double the dose of one active drug but not the other, the tablet of the invention could meet that need. Alternatively, if a patient were to develop a need to ingest only one active drug, possibly temporarily, due to such conditions as blood pressure changes or a side effect to one drug but not the other, the tablet of the invention allows this to be done without a new dosage form being prescribed.

3. Another use of the invention involves the combination of amlodipine and chlorthalidone or another diuretic, which may usefully be combined to treat hypertension. Benefits of the invention are similar to those described in the paragraph immediately preceding this paragraph.

4. Another use of the invention involves the combination of olmesartan medoxomil (olmesartan, an angiotensin receptor blocker) and hydrochlorothiazide (HCTZ). This product is currently marketed in the United States under the name Benicar/HCT®, with the doses, respectively, of, in mg: 20/12.5, 40/12.5, and 40/25. A very common starting dose of a patient will be 20/12.5 once daily. The product is currently marketed in all strengths as a homogeneous tablet containing both active drugs. Formulated according to the current invention, a patient who begins treatment with the 20/12.5 dose may be increased with the same tablet to each of the other doses by ingesting one whole 20/12.5 tablet and either a half tablet containing 20 mg of olmesartan or a half tablet containing 25 mg of HCTZ. This will provide the physician an opportunity to investigate the new dose before giving the patient a new prescription. Other advantages of the invention are similar to those described above.

5. Another useful combination product that may he formulated according to the invention involves angiotensin converting enzyme inhibitors (ACEs) and diuretics such as HCTZ. Both types of drug not uncommonly have side effects, so that the invention will be useful to physicians in dealing with the side effects, as well as with changing dosing needs to deal with the anti-hypertensive and other clinical benefits of the drugs.

6. Another product that may benefit from the invention regarding separating active drugs in separate outer layers with an inactive middle segment (layer) is a combination product containing two active drugs, fluoxetine and olanzapine.

No limitation to the above therapeutic fields or to the specific examples within their fields is intended for tablets of the invention, which may be used in any suitable combination of drugs. No limitation to two-drug combinations exists, as well. For instance, one outer active segment of a tablet according to the invention could contain levodopa and carbidopa, and the other outer active segment could contain entacapone, a tablet product containing all three drugs in a homogeneous fashion that is currently marketed in the United States as Stalevo®. Also, a tablet per the invention could involve five layered segments, with, for example, amlodipine in one outer segment, an inactive segment adjoining it, a middle segment containing chlorthalidone or HCTZ, and a second inactive Segment adjoining both it and the other outer segment that contains benazepril (see FIG. 5). If both inactive segments were of adequate dimensions to be conveniently breakable without damaging any of the three active segments, thus providing significant clinical advantages due to the adoption of flexible dosing of the different active segments.

The following list of possible combinations of a plurality of drugs is exemplary and not limiting. The combinations referred to may include two or more members of the classes listed. Drugs listed below, and herein, may for convenience exclude mention of any salt of a drug; e.g., "atorvastatin" is listed even though its marketed form is atorvastatin calcium.

Without limitation, useful combinations may include a plurality of drugs from within the following six drug classes.

In addition, tablets of the invention may be created containing only one drug from the following list. With regards to combination use, two methods of use may apply to the invention. One of these methods is to place an individual drug in a granulation and a different individual drug (or combination of drugs) in a different granulation, potentially with an inactive granulation interposed between them; another method is to place a plurality, of drugs in one or more segments.

1. Anti-anginal agents, for example:
   A. Calcium antagonists (see list below);
   B. Beta-blocker (see list below);
   C. Organic nitrate preparation (e.g., isosorbide mononitrate or dinitrate).
2. Anti-anginal agent plus an anti-platelet agent, such as aspirin, clopidogrel, or ticlopidine.
3. Two hypoglycemic agents (see list below).
4. Potassium chloride and any thiazide-type or loop diuretic (see lists below).
5. Lipid-lowering agent plus: hypoglycemic agent, anti-platelet agent, anti-anginal agent, and/or antihypertensive agent (see lists above aid below)
   Hypoglycemic agents include: thiazolidinediones: pioglitazone, rosiglitazone; sulfonylureas: glyburide, glipizide, glimepiride, chlorpropamide;
   Biguanides: metformin;
   Meglitinides: nateglinide, repaglinide:
   Gilucosidase inhibitors: acarbose, miglitol.
6. Antihypertensive agents:
   Beta-blockers: acetbutolol, atenolol, bisoprolol, celiprolol, metoprolol, mebivolol, carvedilol (a mixed alpha-beta blocker), nadolol, oxpreniolol, penbutolol, pindolol, propranolol, timolol, betaxolol, carteolol;
   Calcium antagonists (calcium-channel blockers): nifedipine, amlodipine, verapamnil, diltiazein, nisoldipine, felodipine, isradipine, lacidipine, lercanidipine, nicardipine, manidipine;
   Thiazide-type diuretics (with or without potassium-retaining diuretics such as triamterene, amiloride, or spironolactone): hydrochlorothiazide, chlorothiazide, cyclopenthiazide, polythiazide, bendrofluazide, hydroflumethiazide, chlorthalidone, indapamide, methylclothiazide, metolazone;
   Angiotensin converting enzyme inhibitors: captopril, enalapril, lisinopril, ramipril, trandolapril, quinapril, perindopril, moexipril, benazepril, fosinopril;
   Angiotensin receptor blockers: losartan, valsartan, candesartan, telmisartan, eprosartan, irbesartan:
   High-ceiling (loop) diuretics (with or without potassium-retaining diuretics such as triamterene, amiloride, or spironolactone): furosemide, tortsemide, ethacrynic acid, bumetamide;
   Aldosterone antagonist diuretics: spironolactone, eplerenone;
   Alpha-blockers: doxazosin, terazosin, prazosin, indorarmin, labetolol (a mixed alpha-beta blocker);
   Central alpha-agonists: clonidine, methyldopa:
   Imidazoline: moxonidine;
   Direct vasodilators: hydralazine, minoxidil;
   Adrenergic neuronal blocker: guanethidine.
   Lipid-lowering agents include:
   Statins: lovastatin, simvastatin, pravastatin, rosuvastatin, atorvastatin, fluvastatin;
   Fibrates: clofibrate, bezafibrate, fenofibrate, gemfibrozil, ciprofibrate;
   Others: ezetimide, niacin, acipimox.

The combinations of drugs disclosed herein are for illustrative purposes and are not intended to limit the scope of the invention.

Regarding the important usage of the tablets and tablettes of the invention, that involving division of a tablet into tablettes containing similar active segments, most drugs that may undergo dosage adjustment will be preferred if they may be divided in an optimally precise manner. Examples of drugs that will especially benefit from the advances of the invention in this manner include narrow therapeutic index drugs such as warfarin, digoxin, L-thyroxine; vasoactive drugs such as amlodipine; hypoglycemic agents such as rosiglitazone and glipizide; and anxiolytics drugs such as alprazolam. These are, however, but a small fraction of the great number of drugs that will benefit from the various embodiments and procedures of the invention.

There are numerous methods of use of the dosage forms of the invention, including its tablets and tablettes. Persons skilled in the medical and pharmaceutical arts will recognize the many advantages that the various embodiments of the invention allow over current products. Some examples of benefits of the inventions involving tablets containing exactly one similar active segment are described immediately below.

1. Warfarin is an anticoagulant marketed in the U.S. under the brand name Coumadin®, which is a scored tablet. Research has shown that patients do not break warfarin 5 mg tablets into equal 2.5 mg segments. The invention teaches different types of tablets that allow warfarin tablets of any common human dose to be broken into precise halves, and potentially precise thirds, quarters. etc. Thus a patient may utilize warfarin half-tablets produced as per the invention with similar confidence as in the whole tablet. Because warfarin doses are frequently broken, many clinical scenarios exist in which the invention will benefit patients.

2. Norvasc (amlodipine besylate or amlodipine herein) is marketed as unscored 2.5, 5, and 10 mg tablets in the U.S. These tablets are of irregular shape and are difficult to break. The FDA-approved dosage range is from 2.5 to 10 mg ingested orally daily. The invention allows improved functionality of amlodipine. For example, under the invention, a patient receiving 5 mg daily who a physician wishes to increase to 7.5 mg daily may simply utilize a tablet of the invention that comprises two separate 2.5 mg segments to increase the dose to precisely 7.5 mg, such as by ingesting one whole 5 mg tablet and one 2.5 mg tablette created by breaking a 5 mg tablet into two tablettes each containing 2.5 mg of amlodipine. Convenience and cost savings are clear. Similarly, a patient receiving a 10 mg dose of Norvasc® who is advised to reduce the dose to 5 mg daily must currently purchase a new prescription for 5 mg Norvasc® tablets. The invention provides the ability to provide a 10 mg tablet that may be broken into two tablettes, each containing precisely 5 mg of amlodipine. The invention may therefore enable greater flexibility in treating patients, and provide cost savings as well. A further benefit of the invention is that various embodiments allow fully accurate separation of a tablet into a tablette comprising one-fourth of the dose of the active ingredient as is found in the whole tablet. This may for example be done for amlodipine by providing four active segments all containing 2.5 mg of amlodipine and all contiguous with the same side of an inactive outer segment (see embodiment #1; and see FIG. 6a modified to have four and not two active segments). Thus, a 10 mg amlodipine tablet of the invention may be utilized to provide a 7.5 mg dose; or, it may be utilized to provide four 2.5 mg doses.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg daily.

Another use of the invention is to for the first time enable a method of cost savings to insurers and patients. The invention allows this because many drugs, such as Norvasc® and Coumadin®, have pricing that differs little (if at all) between different doses. Because tablet splitting is imprecise for most scored tablets, the practice of mandatory splitting has been met with disapproval by most physician and pharmacist organizations. The invention enables tablet splitting to provide accurate dosing when a tablet (or some tablettes), as in FIG. 1b) of the invention are broken as described herein. Substantial benefits are foreseen from this innovation. In addition, the ability to separate one active drug from another in a combination product has cost saving advantages, as well.

It is recognized that related inventions may be within the spirit of the disclosures herein. Also no omission in the current application is intended to limit the inventors to the current claims or disclosures. While certain preferred and alternative embodiments of the invention have been set forth for purposes of disclosing the invention, modifications to the disclosed embodiments may occur to those who are skilled in the art.

The invention claimed is:

1. A taller-than-wide pharmaceutical tablet having a height and width wherein the height exceeds the width of said tablet, said height being measured vertically from the top to the bottom of said tablet while it is in the tablet die in which it is fully compressed, after said compression has been completed, and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said taller-than-wide tablet comprising a plurality of layers compressed to form a segmented tablet comprising at least two active segments each comprising at least one active pharmaceutical ingredient, and an inactive segment between said at least two active segments, said inactive segment thereby forming a breaking segment which can be broken through to divide the tablet into discrete portions, each portion containing an intact active segment.

2. The pharmaceutical tablet of claim 1, said tablet further comprising a pharmaceutically acceptable coating that has substantially no effect on release kinetics of a drug contained within the coated tablet as compared to the release kinetics of the drug in an uncoated tablet.

3. The tablet of claim 1 wherein said coating comprises a composition that dissolves rapidly in vivo.

4. The pharmaceutical tablet of claim 1, wherein said active segments form a top end segment and a bottom end segment wherein each of said active end segments comprise at least one pharmaceutically active ingredient.

5. The pharmaceutical tablet of claim 4 wherein said top end segment comprises at least half a minimum therapeutic dose of the at least one active pharmaceutical ingredient contained therein.

6. The pharmaceutical tablet of claim 4 wherein said bottom end segment comprises at least half a minimum therapeutic dose of the at least one active pharmaceutical ingredient contained therein.

7. The pharmaceutical tablet of claim 4 wherein said top end segment and bottom end segment each comprise at least half a minimum therapeutic dose of the at least one active I pharmaceutical ingredient contained in each respective end segment.

8. The pharmaceutical tablet of claim 4 wherein said top end segment comprises at least a therapeutic dose of the at least one active pharmaceutical ingredient contained therein.

9. The pharmaceutical tablet of claim 4 wherein said bottom end segment comprises at least a therapeutic dose of the at least one active pharmaceutical ingredient contained therein.

10. The pharmaceutical tablet of claim 4 wherein said top end segment and said bottom end segment each comprise at least a therapeutic dose of the at least one active pharmaceutical ingredient contained therein.

11. The pharmaceutical tablet of claim 4 wherein the top end segment and the bottom end segment each comprises the same active pharmaceutical ingredient.

12. The pharmaceutical tablet of claim 4 wherein each end segment comprises a different active pharmaceutical ingredient.

13. The pharmaceutical tablet of claim 4 wherein said top end segment and said bottom end segment contains an equal amount of an active pharmaceutical ingredient.

14. The pharmaceutical tablet of claim 13 wherein the equal amounts of active pharmaceutical ingredient in said top end segment and said bottom end segment total at least a minimum therapeutic quantity of said active pharmaceutical ingredient.

15. The pharmaceutical tablet of claim 14 wherein the top end segment and the bottom end segment each contains at least a minimum therapeutic amount of said active pharmaceutical ingredient.

16. The pharmaceutical tablet of claim 4 wherein said active pharmaceutical ingredient is selected from the group consisting of an anti-anginal agent, a calcium antagonist, a beta-blocker, an organic nitrate preparation, an anti-platelet agent, aspirin, clopidogrel, ticlopidine, a hypoglycemic agent, potassium chloride, a thiazide-type diuretic, a loop diuretic, a lipid-lowering agent, a hypoglycemic agent, a thiazolidinedione, pioglitazone, rosiglitazone, a sulfonylurea, glyburide, glipizide, glimepiride, chlorpropamide, a biguanide, metformin, a meglitinide, nateglinide, repaglinide, a glucosidase inhibitor, acarbose, miglitol, an antihypertensive agent, acebutolol, atenolol, bisoprolol, celiprolol, metoprolol, mebivolol, carvedilol, a mixed alpha-beta blocker, nadolol, oxprenolol, penbutolol, pindolol, propranolol, timolol, betaxolol, carteolol, nifedipine, amlodipine, verapamil, diltiazem, nisoldipine, felodipine, isradipine, lacidipine, lercanidipine, nicardipine, manidipine, triamterene, amiloride, spironolactone, hydrochlorothiazide, chlorothiazide, cyclopenthiazide, polythiazide, bendrofluazide, hydroflumethiazide, chlorthalidone, indapamide, methylclothiazide, metolazone, an angiotensin converting enzyme inhibitor, captopril, enalapril, lisinopril, ramipril, trandolapril, quinapril, perindopril, moexipril, benazepril, fosinopril, an angiotensin receptor blocker, losartan, valsartan, candesartan, telmisartan, eprosartan, irbesartan, ethacrynic acid, bumetamide, an aldosterone antagonist diuretic, eplerenone, an alpha-blocker, doxazosin, terazosin, prazosin, indoramin, labetolol, a central alpha-agonist, clonidine, methyldopa, imidazoline, moxonidine, a direct vasodilator, hydralazine, minoxidil, an adrenergic neuronal blocker, guanethidine, a statin, lovastatin, simvastatin, pravastatin, rosuvastatin, atorvastatin, fluvastatin, a fibrate, clofibrate, bezafibrate, fenofibrate, gemfibrozil, ciprofibrate, ezetimibe, niacin, and acipimox.

17. The pharmaceutical tablet of claim 4 wherein the tablet further comprises at least one segment in addition to the top end segment and the bottom end segment, said at least one additional segment has substantially no effect on release kinetics of any drug contained within the top end segment and the bottom end segment.

18. The pharmaceutical tablet of claim 4 wherein each segment is an immediate release composition.

19. The pharmaceutical tablet of claim 5 wherein said top end segment and said bottom end segment are controlled release compositions selected from the group consisting of a matrix composition and a microencapsulation composition.

20. The pharmaceutical tablet of claim 19 wherein said controlled release composition is a matrix composition.

21. The pharmaceutical tablet of claim 19 wherein said controlled release composition is a microencapsulation composition.

22. The pharmaceutical tablet of claim 19 wherein said top end segment and said bottom end segment comprise the same active pharmaceutical ingredient in the same controlled release composition.

23. The pharmaceutical tablet of claim 19, said tablet further comprising a middle segment comprising a composition that has substantially no effect on release kinetics of a drug contained within the top end segment and the bottom end segment.

24. The pharmaceutical tablet of claim 23 wherein said middle segment is a substantially inactive segment that is substantially free of active pharmaceutical ingredient.

25. The pharmaceutical tablet of claim 4 wherein said tablet further comprises at least one score.

26. The pharmaceutical tablet of claim 23 wherein said at least one score is positioned substantially transverse to the vertical axis of said tablet.

27. The pharmaceutical tablet of claim 23 wherein said score is located in one segment selected from the group consisting of a top end segment, a middle segment, and a bottom end segment.

28. The pharmaceutical tablet of claim 1 wherein said tablet is substantially free of an exit port formed in the tablet at the time of manufacture for releasing active pharmaceutical ingredient.

29. The pharmaceutical tablet of claim 1 wherein said tablet is substantially free of a composition that swells or forms a gel.

30. The pharmaceutical tablet of claim 1, wherein the inactive segment may be readily broken through to provide substantially equal amounts of a drug or drugs in each of the two tablettes formed by said breaking.

31. The pharmaceutical tablet of claim 4 wherein said tablet further comprises a middle, substantially inactive segment substantially free of active pharmaceutical ingredient, said middle segment providing a breaking region for said tablet for breaking through said middle segment while leaving the top end segment and bottom end segment substantially intact, wherein breaking of the middle segment creates substantially equal amounts of the pharmaceutical active ingredient in the top end segment and the bottom end segment.

* * * * *